United States Patent [19]

Emmons et al.

[11] 4,088,674

[45] May 9, 1978

[54] NOVEL ESTER ISOCYANATES

[75] Inventors: William D. Emmons, Huntingdon Valley; Jerome F. Levy, Bethayres, both of Pa.

[73] Assignee: Rohm and Haas Company, Philadelphia, Pa.

[21] Appl. No.: 254,809

[22] Filed: May 12, 1972

Related U.S. Application Data

[62] Division of Ser. No. 841,128, is a division of Ser. No. 519,001, Jan. 6, 1966, Pat. No. 3,468,934.

[51] Int. Cl.$^2$ .............. C07C 119/042; C07C 149/20; C07C 149/40; C07C 163/00

[52] U.S. Cl. .............................. 560/154; 260/404; 560/180; 560/182; 560/16; 560/60; 560/118; 560/17; 560/61; 560/87; 560/80; 560/81; 560/110

[58] Field of Search ............. 260/481 R, 485 J, 484 P

[56] References Cited

U.S. PATENT DOCUMENTS

| | | | |
|---|---|---|---|
| 2,469,317 | 5/1949 | Shokal et al. | 260/484 P |
| 2,729,676 | 1/1956 | MacPeek et al. | 260/485 J |
| 3,275,679 | 9/1966 | Brotherton et al. | 260/475 R |
| 3,454,606 | 7/1969 | Brotherton et al. | 260/481 R |

FOREIGN PATENT DOCUMENTS

| | | | |
|---|---|---|---|
| 633,465 | 1/1963 | Belgium | 260/485 J |
| 723,173 | 12/1965 | Canada | 260/485 J |

*Primary Examiner*—Vivian Garner

[57] ABSTRACT

This invention concerns novel ester isocyanates derived from acyloxyalkylamine hydrochlorides. The novel compounds may contain a hetero atom in either the acid or alkanolamine moiety and may contain oxalic acid as the acyl moiety.

2 Claims, No Drawings

NOVEL ESTER ISOCYANATES

This is a division of application Ser. No. 841,128 filed July 11, 1969, now U.S. Pat. No. 3,705,189, granted Dec. 5, 1972, which is a divisional application of our earlier filed and copending application Ser. No. 519,001, filed Jan. 6, 1966, now U.S. Pat. No. 3,468,934, granted Sept. 23, 1969, and entitled "Method of Preparing Acyloxyalkylamine Hydrochlorides and Novel Compounds Produced Thereby."

This invention relates to a novel process for the preparation of acyloxyalkylamine hydrochlorides and to novel amine hydrochlorides and isocyanates prepared by this process.

Acyloxyalkylamine hydrochlorides are valuable intermediates in the preparation of other compounds. They are of particular use in preparing isocyanates by phosgenation. The acyloxyethylamine hydrochlorides can be used to make the corresponding N-hydroxyethylamides. Moreover, the dibasic acyloxyalkylamine hydrochlorides themselves can be used as curing agents for epoxy resins and can be reacted with formaldehyde and formaldehyde-containing materials, such as urea-formaldehyde resins. Accordingly, the art has long been interested in finding a commercially practicable means of synthesizing these compounds.

Heretofore, only a few types of acyloxyalkylamine hydrochlorides have been described in the literature and those were prepared by expensive and uneconomical processes. Further, even by the use of the expensive synthesis techniques available, some of the acyloxyalkylamine hydrochlorides could not be prepared successfully. Thus, heretofore the art has taught that to produce the desired acyloxyalkylamine hydrochlorides it is necessary to react the alkanolamine hydrochloride with either an acid chloride or acid anhydride rather than the much cheaper and more readily available acid. Moreover, the art does not show the successful synthesis of an acyloxyalkylamine or salt thereof: (a) which contains a hetero atom in either the acid or alkanolamine moiety or (b) which uses oxalic or malonic acid as the acyl moiety. Also, while the art does disclose the preparation of an acyloxyalkylamine using an hydroxyamine other than ethanolamine, the same art also teaches that the product cannot be successfully phosgenated to produce the corresponding isocyanate.

Wystrach et al in U.S. Pat. No. 2,626,278 describe the preparation of monoacyloxyethylamine hydrochlorides and the corresponding isocyanates by first converting ethanolamine to the hydrochloride by direct reaction with hydrochloric acid, converting the appropriate monocarboxylic acid to its anhydride or acid chloride, and then reacting the ethanolamine hydrochloride with the anhydride or acid chloride in an inert liquid with a suitable catalyst. The isocyanates are produced by phosgenating the amine hydrochloride. The extra cost entailed in using the acid anhydride or acid chloride to date has prevented the commercial exploitation of these compounds. Moreover, Wystrach et al teach that their process is specific to the use of ethanolamine and that when other alkanolamines as, specifically, propanolamine, are used, the result is a viscous uncharacterized product which presumably contains the appropriate acyloxypropanolamine hydrochloride but which cannot be successfully phosgenated to produce the isocyanate.

More recently, Brotherton et al in Belgian Pat. No. 633,465 disclose, inter alia, the preparation of amine hydrochlorides and the corresponding isocyanates by reacting the acid chloride of the selected dibasic acid with the desired hydroxyamine salt using precisely the same process described by Wystrach et al. Also as in Wystrach et al, the isocyanates are prepared by the straightforward phosgenation of the amine hydrochlorides. Unlike Wystrach et al, Brotherton et al describe the use of alkanolamines generally, including propanolamine. However, there is no example in Brotherton et al showing the operability of any hydroxyamine other than ethanolamine.

When the carboxylic acid groups of a dicarboxylic acid are separated by more than two carbon atoms, the carboxyl radicals have little influence on each other and each behaves chemically as if they were separate carboxylic acids. However, the lowest members in the dibasic acid series, namely oxalic acid and malonic acid, differ from the remainder of the series in that the close proximity of the carboxyl groups to each other leads to a significant interaction therebetween modifying the properties of the compound. In particular, both of these acids are easily decomposed, particularly when in the presence of strong acids at moderately high temperatures. Nevertheless, Brotherton et al teach that alkanolamine hydrochlorides can be successfully reacted with malonic acid using the acid chloride, although there is no teaching of the possibility of using oxalic acid, i.e., Brotherton et al require at least one carbon atom to separate the carboxyl groups. Although Brotherton et al thus disclose the operability of malonic acid, there is no example showing the operability of this compound.

Now, in accordance with the instant invention, a process has been found for the direct reaction of a free acid and an alkanolamine hydrochloride to produce the corresponding acyloxyalkylamine hydrochlorides. The process eliminates the use either of an acid chloride or an acid anhydride and at the same time suppresses side reactions which interfere with the desired result. This surprising and unexpected result has been obtained by passing a stream of hydrogen chloride through a reaction medium of the desired carboxylic acid, alkanolamine hydrochloride and inert liquid while the reaction between the alkanolamine hydrochloride and the acid is occurring. Mixtures of acids and/or alkanolamines may be used, if desired, to produce a mixture of the corresponding amine hydrochlorides. Surprisingly, it has been found possible to produce amine hydrochlorides and isocyanates not heretofore obtainable, such as those derived from oxalic acid. Moreover, the present process produces amine hydrochlorides from alkanolamines other than ethanolamine which amine hydrochlorides can be successfully phosgenated to produce the corresponding isocyanates.

The alkanolamines which may be used in the instant invention contain from 2 to 8 carbon atoms, have one primary or secondary hydroxyl group and one primary amino group, and may include one hetero oxygen or sulfur atom in the alkyl chain. The alkyl group of the alkanolamine may be substituted with inert substituent groups as alkyl, phenyl, nitro, halogen, etc. Particularly preferred alkanolamines are ethanolamine, 2-(2-aminoethoxy)-ethanol, 1-amino-2-propanol, 2-amino-1-propanol, 2-methyl-2-amino-1-propanol, 3-amino-1-propanol, and 2-amino-1-butanol. The ability of the present process to economically utilize a variety of alkanolamines permits the production of a variety of acyloxyalkylamine hydrochlorides wherein the amine group may be attached to a carbon which can be primary, secondary or tertiary. The isocyanates produced from these products will, in turn, offer a wide range of reactivities.

The acids which may be reacted directly with the said alkanolamines in the process of the invention are monocarboxylic acids having at least two carbon atoms, oxalic acid, succinic acid and dibasic acids wherein the two carboxyl groups are separated by a divalent aliphatic or alicyclic or aromatic group, the divalent group having at least three atoms between the carboxyl groups, one of which atoms may be a hetero atom. The following acids are illustrative of those which may be used in the present invention: any of the monocarboxylic acids described by Wystrach et al in U.S. Pat. No. 2,626,278; benzoic acid, the toluic acids; aliphatic $\alpha,\omega$-dicarboxylic acids having at least five carbon atoms as glutaric, adipic, sebacic, etc.; alicyclic dicarboxylic acids as 1,4-cyclohexanedicarboxylic acid; aromatic dicarboxylic acids as isophthalic acid, terephthalic acid, diphenic acid, 4,4'-diphenic acid, the phenylene diacetic acids, and 2,7-naphthalenedicarboxylic acid (it should be noted that o-phthalic acid does not have at least three atoms separating the carboxylic groups, and thus is not included); dibasic acids containing a hetero atom as dinicotinic acid, diglycolic acid, thiodiacetic acid, p,p'-oxydibenzoic acid; the thiodialkanoic acids produced by reacting hydrogen sulfide with two moles of an unsaturated acid such as acrylic, methacrylic, crotonic, cinnamic, etc.; and the thiodialkanoic acids produced by reacting sodium sulfide and an ester of a halogenated acid. The oxygen and selenium analogs of these thiodialkanoic acids can also be used. In addition to these general classes of acids which may be used, both oxalic and succinic acids have been found to be operable. Further, the acids may contain substituents which do not interfere with the reaction of this invention. Such substituents include, for example, alkyl groups, aromatic groups, halogen groups as fluorine, chlorine, etc., nitro groups, etc. Examples of such acids are $\alpha$-butylglutaric acid, $\alpha.\beta$-diethylsuccinic acid, p-chlorobenzoic acid, $\beta$-chloroglutaric acid, etc. Mixtures of acids and/or alkanolamines may be used.

In preparing the amine hydrochlorides in accordance with the instant invention, the alkanolamine is first converted to its acid salt, preferably the hydrochloride. The resulting alkanolamine hydrochloride is then reacted with the carboxylic acid in the presence of an inert liquid. The carboxylic acid and the alkanolamine hydrochloride must have a significant solubility in each other under reaction conditions or else the inert liquid used as the reaction medium must be a mutual solvent for these materials. Where one of the reactants is a liquid or is molten under the reaction conditions, an excess of such reactant may be used as the reaction medium so long as such excess does not cause polymerization or promote other undesirable side-reactions, i.e., such excess must act as an inert liquid.

At room temperature, the reaction between the materials is too slow to be of practical significance. Generally, the reaction is carried out between about 40° C. and a temperature not higher than that at which the alkanolamine hydrochloride dissociates into the free amine under the conditions used (i.e., of pressure and other reactants present in the mixture). Generally, the reaction temperature will be from about 50° to 150° C. Water is removed as the reaction progresses as by distillation with a liquid such as benzene which forms an azeotrope with the water. While the reactants are maintained at reaction temperature, a stream of hydrogen chloride gas is passed through the reaction mixture. If desired, the flow of gas may be initiated before the reactants reach the desired reaction temperature or, alternatively, the gas need not be passed through the mixture until after the desired reaction temperature has been reached. Pressure is not critical. Generally, atmospheric pressure is preferred, but pressures either higher or lower than atmospheric may be used.

Where the acyloxyalkylamine hydrochloride is to be converted to the corresponding isocyanate, the conversion is carried out with phosgene or other carbonyl dihalide. The phosgene may be employed in either liquid or gaseous form. The ability to form isocyanates previously taught as impossible is not understood, but may be due to the instant esterification process producing a purer acyloxyalkylamine hydrochloride, i.e., one having lower concentration of undesired by-products, than the prior art process based on the use of an acid chloride or acid anhydride. In the phosgenation reaction, the acyloxyalkylamine hydrochloride is dispersed in an inert, liquid reaction medium, phosgene added, preferably in excess of that needed to react quantitatively with the amino groups, and the temperature of the reaction medium maintained from 100° to 225° C. The molar ratio of phosgene: amine hydrochloride group may be from 1.1:1 to 10:1 and preferably is at least 2:1. Suitable liquid reaction media include aromatic hydrocarbons, chlorinated aromatic hydrocarbons, chlorinated aliphatic hydrocarbons, chlorinated alicyclic hydrocarbons, etc. The phosgenation may also be carried out in steps. The reaction product of the carboxylic acid-alkanolamine hydrochloride reaction may be used as such for the phosgenation, or, if desired, the acyloxyalkylamine hydrochloride may first be purified and the purified product phosgenated.

Representative uses of the acyloxyalkylamine hydrochlorides of the invention are disclosed supra. The isocyanates produced therefrom may be used as cross-linking agents for polymers containing active hydrogen groups, may be reacted with low molecular weight polymers containing active hydrogen groups such as hydroxyl-terminated polyesters or polyethers to produce polyurethanes, and may be added to polymeric compositions to improve the adhesion thereof to a variety of substrates, particularly metallic substrates. They are also useful as intermediates in producing other novel compounds useful as insecticides, herbicides, etc. The monoisocyanates are useful as modifying agents for cellulose, starch, polyvinyl alcohol, algin, copolymers of hydroxyalkyl esters of unsaturated acids, etc. Thus, the isocyanates produced byphosgenating the reaction product of an alkanolamine — higher fatty acid may be used as a chemical sizing agent on paper, as waterproofing materials for textiles, etc.

The following examples are by way of illustration and not of limitation. All parts are by weight unless otherwise specified.

EXAMPLE 1

A four-necked, round-bottomed flask, fitted with a mechanical stirrer, a thermometer, a gas inlet tube, and a Dean-Stark trap, was charged with 61 g. (1.00 mole) of ethanolamine and 350 ml. of m-cresol. Hydrogen chloride was passed in through the gas inlet tube to convert the ethanolamine to the hydrochloride salt, then 284.5 g. (1.00 mole) of stearic acid was charged. The reaction mixture was heated to 120° C., then benzene was added until the mixture was refluxing at that temperature. The reaction mixture was refluxed for 7 hours while a stream of hydrogen chloride was being passed in. At the end of this period, the theoretical amount of water had been collected. The reaction mixture at this point was an oil which solidified on cooling. After two recrystallizations from isopropanol the yield was 209.0 g., corresponding to 58% of theoretical, m.p. 113°-115° C.

Anal. calc'd for $C_{20}H_{42}ClNO_2$: C, 65.99%; H, 11.63%; Cl, 9.74%; N, 3.85%

Found: C, 65.77%; H, 11.63%; Cl, 10.03%; N, 4.04%.

EXAMPLE 2

A three-necked, round-bottomed flask fitted with a mechanical stirrer, a Dean-Stark water separator trap and a gas-inlet tube, was charged with 22.5 g. (0.25 mole) of oxalic acid, 49 g. (0.50 mole) of ethanolamine hydrochloride and 400 ml. of 1,2-dichloroethane. The reaction mixture was heated at reflux while a slow stream of hydrogen chloride was passed into the reaction mixture. After a total of 15 hours of reflux, water azeotroping has ceased. During this period, it was often necessary to break up the solid in the flask. The filtered product was dried in a vacuum oven to give 59 g. of crude di-$\beta$-aminoethyl oxalate dihydrochloride, m.p. 175°-180° C. The yield corresponds to 95% of the theoretical.

Anal. calc'd for $C_6H_{14}Cl_2N_2O_4$: Cl, 28.47%.
Found: Cl, 28.07%.

EXAMPLE 3

The apparatus of Example 2 was charged with 195 g. of ethanolamine hydrochloride (2.0 moles), 146 g. of adipic acid (1.00 mole) and 1.1 of toluene. The mixture was heated at reflux while a slow stream of hydrogen chloride, (0.043 mole/hr.) was passed in. After about 26 hours of refluxing production of water had ceased and 41 ml. of approximately 10 N hydrochloric acid had been collected in the azeotrope trap. In the initial stages of the esterification the reaction mixture consisted of two phases, with the lower phase a mutual solution adipic acid, ethanolamine hydrochloride and product. The upper phase was toluene. About halfway through the reaction the lower phase began to solidify. The product, after being removed by filtration and dried, weighed 296.5 g. corresponding to 97% of theory, m.p. 195°-200° C.

EXAMPLE 4

As in Example 3 using toluene as the reaction medium, di-$\beta$-aminoethyl azelate dihydrochloride was prepared in 90% yield. The product had a melting point of 171°-180° C. After two recrystallizations from ethanol, the melting point was raised to 198°-199° C.

EXAMPLE 5

This example illustrates the use of a solvent as the diluent for the esterification reaction instead of a nonsolvent as had been the case in Examples 2 and 3.

The apparatus of Example 1 was charged with 610.8 g. (10 moles) of ethanolamine and 508.7 g. of o-cresol. Then 10 moles of anhydrous chloride was passed in, following which 730.7 g (5 moles) of adipic acid was charged. The reaction mixture was heated to 115° C. adding enough benzene (130 mls.) to maintain a good rate of reflux at that temperature. With gaseous hydrogen chloride being passed in at the rate of 100 ml./min., the reaction mixture was heated at reflux until the theoretical amount of water (as an aqueous hydrochloric acid solution) had been collected. This required 17.5 hours. Periodically during this interval, benzene had to be added to maintain refluxing at 110°-120° C. Some of the product began to crystallize out of solution in the later stages of the reaction. Finally, the reaction mixture was diluted with a large quantity of benzene, filtered, and then digested with isopropanol to remove most of the remaining cresol. The product after filtration and drying had a m.p. of 207°-210° C. (pure product melts at 221° C.).

EXAMPLE 6

This example illustrates the necessity of using excess hydrogen chloride while conducting the esterification reaction.

The apparatus of Example 1 was charged with 73.0 g. (0.50 mole) of adipic acid, 97.5 g. (1.0 mole) of ethanolamine hydrochloride, 450 ml. of o-dichlorobenzene, and 175 ml. of benzene. The mixture was heated to reflux (116°-118°) and was kept at this temperature while the water produced by the reaction was collected in the trap. Periodically, this water was removed, and titrated with N/10 sodium hydroxide to determine the amount of hydrogen chloride which had been lost from the reaction mixture. These data indicate that hydrogen chloride was being evolved from the reaction mixture and collected in the azeotrope trap at a uniform rate of approximately 0.25%/hr. of the total hydrogen chloride charged as ethanolamine hydrochloride. After 40 hours by which time approximately the theoretical quantity of water had been collected, 8.4% of the charged hydrogen chloride was accounted for in the water which had azeotroped over. The product at this point was a pasty mass, quite unlike the high melting (ca. 200° C.) crystalline product one obtains if a slight excess of hydrogen chloride is passed into the reaction mixture throughout the esterification. Furthermore, an infrared spectrum of product prepared without the use of excess hydrogen chloride shows peak broadening and the appearance of extraneous peaks, particularly in the region of 5.5–6.5, which suggests the formation of amide containing impurities. Pure $\beta$-aminoethyl adipate dihydrochloride, or the product prepared as described in Examples 3 and 4, displays only two principal absorptions in this region of the infrared: a singlet at 5.8 and a peak with a slight shoulder at 6.3$\mu$.

EXAMPLE 7

The apparatus of Example 1 was charged with 122 g. (2.00 moles) of ethanolamine, 200 ml. of tetramethylene sulfone and 166 g. (1.00 mole) of isophthalic acid. Hydrogen chloride (2.00 moles) was passed in, and, still passing HCl in at the rate of 1.5 mole/hr., the temperature was raised to 150° C. Sufficient benzene was added at this point, and as required later, to maintain a good rate of reflux at this temperature. After a total of 12 hours of reflux, spread over several days, 45.5 ml. of ca. 10 N hydrochloric acid had been collected in the azeotrope trap. The reaction mixture was cooled, diluted with isopropanol and then filtered to give 168 g. of crude di-$\beta$-aminoethyl isophthalate dihydrochloride. Recrystallization from isopropanol gave a pure sample, m.p. 240° C.

Anal. calc'd for $C_{12}H_{18}Cl_2N_2O_4$: C, 44.32%; H, 5.58%; Cl, 21.81%; N, 8.62%. Found: C, 43.91%; H, 5.85%; Cl, 21.25%; N, 8.45%.

EXAMPLE 8

The apparatus of Example 1 was charged with 61.1 g. (1.00 mole) of ethanolamine, 300 ml. of o-dichlorobenzene and 125 ml. of benzene. Then 1.25 moles of dry hydrogen chloride was passed in, followed by the addition of 67.1 g. (0.50 mole) of 2,2'-oxydiacetic acid. The reaction mixture was heated under reflux at 110°–120° while hydrogen chloride was passed in at the rate of 30 ml./min. Additional benzene had to be added from time to time to maintain a good rate of reflux. After a total of 23.5 hours of heating, 21.4 ml. of 10 N hydrochloric acid had been collected in the azeotrope trap. The solvent was decanted and the crude product, a viscous amber-colored oil, was heated 200 ml. of ethanol, whereupon the product crystallized. After cooling, the solid was separated by filtration, washed with more ethanol and dried to give 102.3 g. of di-β-aminoethyl 2,2'oxydiacetic acid dihydrochloride, m.p. 130°–152° C., which corresponds to 35% of the theoretical yield. The infrared spectrum of this product had a doublet carbonyl absorption at 5.65 and 5.75μ.

After two recrystallizations from ethanol the melting point was raised to 186°–187° C., but the infrared spectrum was essentially unchanged from that of unrecrystallized product.

Anal. calc'd for $C_8H_{18}Cl_2N_2O_5$: C, 32.77%; H, 6.19%; Cl, 24.19%; N, 9.56%. Found: C, 32.76%; H, 6.26%; Cl, 23.82%; N, 9.28%.

EXAMPLE 9

Using the process described in Example 8, di-β-aminoethyl sebacate dihydrochloride was produced. The solid, dried product, after two recrystallizations from ethanol, melted at 219°–220° C.

EXAMPLE 10

Using the process described in Example 8, di-b-aminoethyl α-methylglutarate dihydrochloride was produced. At room temperature the product was a thick oil. Analysis for chlorine gave 23.35% against a calculated value of 23.23%.

EXAMPLE 11

The apparatus of Example 1 was charged with 61.1 g. (1.00 mole) of ethanolamine and 450 ml. of o-dichlorobenzene. An excess of hydrogen chloride was passed in to form the hydrochloride, then 75.1 g. (0.50 mole) of thiodiacetic acid was added. The reaction mixture was heated to 115° C. and enough benzene was added to maintain a good rate of refluxing at that temperature. After a total of 14 hours of refluxing during which time a slow stream of hydrogen chloride was passed in, the theoretical amount of water had been collected. The solvent was decanted and the crude product was removed by filtration, washed with benzene and dried to give 154 g. of crude di-β-aminoethyl-2,2'-thiodiacetate, m.p. 118°–154° C.

Anal. calc'd for $C_8H_{18}Cl_2N_2O_4S$: Cl, 22.93%. Found: Cl, 22.54%.

A portion of this material was recrystallized twice from ethanol, m.p. 178°–180° C.

EXAMPLE 12

Using the process described in Example 11, but with toluene as the reaction medium instead of o-dichlorobenzene, di-β-aminoethyl-3,3'-thiodipropionate dihydrochloride was produced in 98% yield. The crude product was an off-white crystalline solid. After recrystallization from ethanol, the product had a melting point of 162°–163° C.

EXAMPLE 13

The apparatus of Example 2 was charged with 119 g. (1.32 moles) of oxalic acid and 374 g. (2.65 moles) of β-(β-aminoethoxy)-ethanol hydrochloride and 1.3 l. of 1,2-dichloroethane. With a slow stream of hydrogen chloride being passed in, the reaction mixture was heated at reflux for a total of 43 hours, collecting the water which azeotroped over. The product was removed by filtration and dried in a vacuum oven to give 434 g. (98% of theoretical) of di-β-(β-aminoethoxy)-ethyl oxalate dihydrochloride, m.p. 135°–140° C.

Anal. calc'd for $C_{10}H_{33}Cl_2N_2O_6$: Cl, 21.03%. Found: Cl, 20.94%.

EXAMPLE 14

The apparatus of Example 2 was charged with 210 g. (2.00 moles) of β-(β-aminoethoxy)-ethanol and 1.5 l. of 1,2-dichloroethane. With cooling, an excess of hydrogen chloride was passed in, then 146 g. (1.00 mole) of adipic acid was added. After a total of 39 hours of refluxing, while still passing in anhydrous hydrogen chloride, the esterification was complete. The filtered product was dried in a vacuum oven to give 386 g. of di-β-(β-ethoxy)-ethyl adipate dihydrochloride corresponding to 98% of the theoretical yield, m.p. 115°–123° C.

Recrystallization twice from ethanol raised the melting point to 133°–134° C.

Anal. calc'd for $C_{14}H_{30}Cl_2N_2O_6$: C, 42.75%; H, 7.69%; Cl, 18.03%; N, 7.12%. Found: C, 43.09%; H, 7.97%; Cl, 17.80%; N, 7.12%.

EXAMPLE 15

A three-necked, round-bottomed flask fitted with a mechanical stirrer, a gas inlet tube and a condenser was charged with 20 g. (0.080 mole) of di-β-aminoethyl oxalate dihydrochloride and 500 ml. of o-dichlorobenzene. The reaction mixture was saturated with phosgene, and then, with the phosgene flow at 0.36 mole/hr., the mixture was heated for 0.5 hr. at 125° C., 1.5 hrs. at 140° C., then heated slowly (over a 2 hr. period) to 180° C. and held there for 0.25 hr. The reaction mixture was cooled, a small amount of dark solid was removed by filtration, and the solvent was distilled under reduced pressure at about 100° C. The product was distilled on a molecular still at 0.5 to 1.0 mm. Hg. pressure with a wall temperature of 200°–220° C. to give 11 g. (60% of theoretical) of a slightly yellow liquid which crystallized on cooling. The infrared spectrum was entirely consistent with the assigned structure of di-β-isocyanatoethyl oxalate. Recrystallization of the product from dichlorobenzene gave material melting at 28°–30° C. which was redistilled, b.p. 140–142 (0.25–0.50 mm.), to give an analytical sample.

Anal. calc'd for $C_8H_6N_2O_6$: C, 42.11% H, 3.53%; Cl, 0.00%; N, 12.27%. Found: C, 41.47%; H, 3.53%; Cl, 0.29%; N, 12.29%.

EXAMPLE 16

The apparatus of Example 15 was charged with 30 g. of di-$\beta$-($\beta$-aminoethoxy)-ethyl oxalate dihydrochloride (0.089 mole) and 300 ml. of o-dichlorobenzene. With phosgene being passed in at the rate of 0.36 mole/hour, the mixture was heated for 2.25 hrs. at 150° C. and then for 1 hr. at 175° C. After the first ten minutes at 175° C., the reaction mixture cleared to an amber solution. After filtering out a small amount of solid, the solvent was distilled off under reduced pressure at about 100° C., and then the product was distilled through a molecular still using wall temperatures of 250°–270° C. (0.25–0.50 mm.). A 49% yield of product was obtained which had a strong band at 4.5 in the infrared (isocyanate). The sample crystallized on being stored in the refrigerator.

EXAMPLE 17

Di-$\beta$-aminoethyl-2,2'-thiodiacetate dihydrochloride was first purified by digesting with isopropanol, cooling, filtering, and repeating this purification step, m.p. 170°–173° C. Then 14.5 g. (0.043 mole) of this purified diamine dihydrochloride were charged along with 100 ml. of o-dichlorobenzene to a four-necked, round-bottomed flask fitted with a mechanical stirrer, a thermometer, a condenser and a gas inlet tube. The mixture was phosgenated at 150° C. for 2 hours (phosgene flow 1.0 mole/hr.) and filtered. The solvent was distilled under reduced pressure to yield as the residue, crude di-$\beta$-isocyanatoethyl-2,2'-thiodiacetate. An infrared spectrum of this material had strong absorptions at 4.4$\mu$(isocyanate) and 5.75$\mu$(ester). There was no 3.9$\mu$ absorption which would have indicated cleavage to a thiol compound. A determination of free isocyanate by titration with butylamine indicated a purity of 86%. A derivative, bis-[$\beta$-(N'-phenylureido)-ethyl]-2,2'-thiodiacetate was prepared by reaction with aniline. After several recrystallizations from isopropanol-water, m.p. 238°–239° C.

Anal. calc'd for $C_{22}H_{26}N_4O_6S$ (the aniline derivative): C, 55.68%; H, 5.52%; N, 11.81%; S, 6.76%. Found: C, 55.58%; H, 5.52%; N, 11.72%; S, 6.64%.

EXAMPLE 18

The apparatus of Example 1 was charged with 73.0 g. (0.5 mole) of adipic acid, 250 ml. of o-dichlorobenzene and 100 ml. of benzene. Then 75.1 g. (1.0 mole) of 3-aminopropanol was added followed by the passage of 1.0 mole of hydrogen chloride into the reaction mixture, cooling so as to keep the temperature of the mixture below 80° C. The mixture was heated to 115° C. adding additional benzene as needed to maintain a good reflux rate at that temperature, hydrogen chloride being passed in at the rate of 0.05 mole/hr. After 10 hours, the theoretical amount of water had been collected, the solvent was decanted and the crude product was recrystallized once from a mixture of isopropanol and water to give 120 g. of product, m.p. 150°–155° C.

Anal. calc'd for $C_{12}H_{26}Cl_2N_2O_4$: Cl, 21.28% Found: Cl, 21.11%. Another recrystallization raised the m.p. to 166°–168° C.

EXAMPLE 19

The apparatus of Example 17 was charged with 66.6 g. (0.2 mole) of di-$\gamma$-aminopropyl adipate dihydrochloride, m.p. 150°–155° C. and 250 ml. of o-dichlorobenzene. This was heated at 150° C. for 3 hours, passing in phosgene at the rate of 1.5 mole/hr. The mixture was decanted and the decantate was stripped of solvent. Then the product was distilled on a wiping film still (wall temperature 260°–275° C., 0.75 mm. pressure). This product was analyzed for isocyanate content by reaction with butylamine, purity 98%.

As shown in Example 6, the use of a stream of HCl throughout the reaction not only catalyzes the desired esterification but also helps to suppress unwanted side-reactions. Thus, the instant process makes possible the production of amino esters with minimum contamination. The ability of the instant process to form the amino esters and isocyanates of dibasic acids containing a hetero atom is highly unusual in view of the general ability of halogen acids to cleave an other-type linkage. As shown in Examples 11 and 12, the thio linkage in particular displays outstanding stability under the reaction conditions.

In addition to phosgenating the amino esters to produce isocyanates as described herein, the amino esters may also be reacted with thiophosgene to produce the corresponding isothiocyanates. Such isothiocyanates are useful in coatings and are of interest as biologically active materials for use as fungicides, herbicides, insecticides, slimicides, etc. as appropriate.

In general, the process of the invention is not applicable to compounds containing reactive double bonds. However, where the reactivity of the double bond is suppressed, as by the presence of blocking groups, the material behaves in this process like a saturated compound and is fully operable. Examples of materials having such "blocked" double bonds are dimer acid and trimer acid. These acids are available from a number of suppliers and are produced by polymerizing unsaturated $C_{18}$ fatty acids. Pure dimer acid is thus a $C_{36}$ aliphatic dibasic acid whose structure is essentially that of a long chain dicarboxylic acid with two or more alkyl side chains. Also within the molecule is a linkage resulting from the polymerization of the two unsaturated fatty acid molecules that form the dimer acid, the nature of the linkage being undetermined. However, its exact position remains obscure. The polymerization reaction also produces an amount of trimer acid, a $C_{54}$ long chain tricarboxylic acid whose structure is correspondingly more complex than that of the dimer acid. If desired, the dimer or trimer acid may be hydrogenated to reduce or eliminate the unsaturation, but this step is not necessary for operability in the process of the invention.

EXAMPLE 20

The acid used as starting material for this preparation was dimer acid (obtained under the trademark Empol 1018). It contains 83% dimer acid and approximately 17% of trimer acid.

The apparatus of Example 1 was charged with 147 g. (0.50 equivalents) of dimer acid, 48.8 g. (0.50 eq.) of ethanolamine hydrochloride, 200 ml. of tetramethylene sulfone and 125 ml. of benzene. The mixture was heated under reflux (ca. 115° C.) with a slow stream of hydrogen chloride being passed in until the theoretical quantity of water had been collected. The reaction mixture was cooled to room temperature, transferred to a separatory funnel and the lower phase (which was predominantly sulfolene and benzene) was withdrawn and discarded. The upper phase was washed well with successive portions of benzene, with the benzene now forming the upper layer, then dried under reduced pressure to give the product as a dark oil. Approximately 75 g. of the oil was added to 300 ml. of o-dichlorobenzene and phosgenated for 6 hours at 135° C., using a phosgene flow rate of 0.5 mole/hr. The o-dichlorobenzene was distilled off under reduced pressure to give a dark oil, the isocyanate content of which was found to be 11.7% NCO by reaction with butylamine. The theoretical value is 11.9% NCO. A portion of this oil was distilled on a wiping film still using a wall temperature of 330° at 0.25–1.0 mm. Hg. pressure.

Anal. Found: C, 72.91%; H, 10.55%; N, 3.85%.

In both the specification and claims, reference is made to passing the hydrogen chloride gas "through the reaction mixture." As is obvious to those skilled in the art, this result may be achieved either by bubbling a stream of hydrogen chloride through the reaction mixture or by initially treating the reaction mixture with hydrogen chloride and then maintaining a flow of hydrogen chloride gas over the surface of the reaction mixture so that the gas passes from the atmosphere within the reaction vessel into the reaction mass itself.

By this means, removal of hydrogen chloride by the azeotroping of the water is compensated for and the reaction medium is kept relatively saturated with hydrogen chloride throughout the esterification reaction.

What is claimed is:

1. An ester represented by the general formula:

$$ZR_1OOC-R_2-X-R_3-COOR_4Z$$

wherein X is a chalcogenide selected from the group consisting of oxygen, sulfur and selenium; $R_2$ and $R_3$ are divalent ($C_1$-$C_2$) alkylene radicals; $R_1$ and $R_4$ are alkylene radicals having from two to eight carbon atoms and up to one hetero oxygen or sulfur atom and Z is —NCO.

2. A compound according to claim 1 wherein $R_1$ and $R_4$ are ethylene groups and $R_2$ and $R_3$ are methylene groups.

* * * * *